United States Patent [19]

d'Hondt et al.

[11] 4,336,353

[45] Jun. 22, 1982

[54] SALTS OF 3-METHYL-2-(2',4'-DIMETHYL-PHENYLIMINO)-4-THIAZOLINE WITH POLYMERS CONTAINING SULFONIC ACID GROUPS

[75] Inventors: Christian d'Hondt, Riehen; Dieter Lohmann, Muttenz; Ernst Neuenschwander, Riehen, all of Switzerland

[73] Assignee: Ciba-Geigy Corporation, Ardsley, N.Y.

[21] Appl. No.: 183,560

[22] Filed: Sep. 2, 1980

[30] Foreign Application Priority Data

Sep. 11, 1979 [CH] Switzerland .......................... 8205/79
Mar. 11, 1980 [CH] Switzerland .......................... 1900/80

[51] Int. Cl.$^3$ ............................................. C08F 8/30

[52] U.S. Cl. ........................................... 525/275; 71/3; 252/106; 424/270; 424/DIG. 8; 525/344; 528/44; 528/171

[58] Field of Search ............... 525/344, 375, 332, 334, 525/333, 335

[56] References Cited

U.S. PATENT DOCUMENTS 3,072,619  1/1963  Turbak ................................ 525/344

*Primary Examiner*—C. A. Henderson
*Attorney, Agent, or Firm*—John Spitals; Frederick H. Rabin

[57] ABSTRACT

Salts of 3-methyl-2-(2',4'-dimethyl-phenylimino)-4-thiazoline with polymers containing sulfonic acid groups, processes for producing them, and their use in combating pests.

2 Claims, No Drawings

SALTS OF 3-METHYL-2-(2',4'-DIMETHYL-PHENYLIMINO)-4-THIAZOLINE WITH POLYMERS CONTAINING SULFONIC ACID GROUPS

The present invention relates to salts of 3-methyl-2-(2',4'-dimethyl-phenylimino)-4-thiazoline with polymers containing sulfonic acid groups, to processes for producing these salts, and to their use in combining pests.

The invention thus relates to salts of the formula

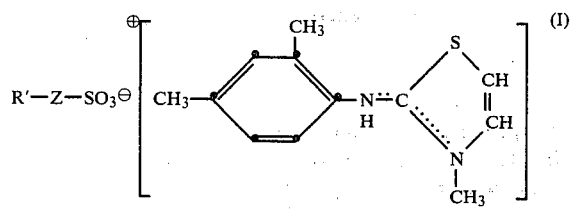

wherein Z is the direct bond or a bridge member, and R' is a polymer, the proportion of the cation being at least 5% relative to the number of recurring structural elements of the polymer.

Preferred bridge members in the case of Z are, inter alia: oxygen or straight-chain or branched-chain alkylene having 1 to 4 C atoms, phenylene or naphthylene each of which is unsubstituted or substituted by halogen atoms, alkyl or alkoxy groups having 1-4 C atoms or by a group —SO$_3^\ominus$M$^\oplus$, or Z is —CH$_2$O—CH$_2$CH$_2$—, —CH$_2$OCH$_2$CH$_2$O—, —CH$_2$SCH$_2$CH$_2$—, —CH$_2$—S—CH$_2$CH$_2$O—, a ring-substituted group

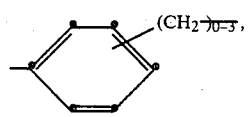

in which the ring is unsubstituted or is substituted by halogen atoms, or by alkyl or alkoxy groups having 1-4 C atoms, or Z is a group

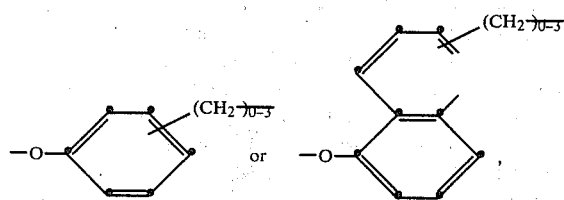

each of which is unsubstituted or substituted by —SO$_3^\ominus$M$^\oplus$, or Z is —COOR$_1$— or —CON(R$_2$)(R$_3$)—, in which R$_1$ is straight-chain or branched-chain C$_3$-C$_8$-alkylene which is unsubstituted or substituted by chlorine or bromine atoms, or interrupted by an oxygen atom, or R$_1$ is cyclohexylene, phenylene, naphthylene, naphthylene substituted by a group —SO$_3^\ominus$M$^\oplus$, or it is C$_2$-C$_4$-alkylene-O-phenylene or

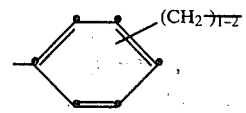

R$_2$ is the direct bond, straight-chain or branched-chain C$_1$-C$_6$-alkylene optionally interrupted by an oxygen atom, or it is straight-chain or branched-chain oxyalkylene having 1-6 C atoms, phenylene, naphthylene, naphthylene substituted by a group —SO$_3^\ominus$M$^\oplus$, C$_1$-C$_4$-alkylene-O-phenylene,

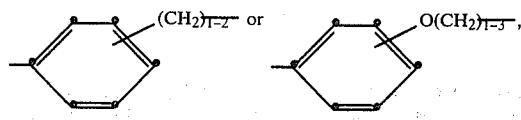

and R$_3$ is hydrogen or C$_1$-C$_6$-alkyl.

The polymers are for example: polyesters, polyester amides, polyamides, polyimides, polyamideimides, polyester imides, polyethers, polyurethanes, polyureas, polycondensation products of phenol, naphthols, melamine and/or urea with aldehydes or ketones, for example formaldehyde, polysaccharides, gelatins, organopolysiloxanes, polyphosphacenes, polymers which are obtained by homo- or copolymerisation of monomers containing multiple bonds, for example C=C double bonds; or by ring-opening polymerisation of saturated or unsaturated aliphatic rings optionally containing hetero atoms. It is also possible to use tanning substances or polymers containing sulfonic acid groups, which are obtained by decomposition or transformation reactions from natural substances, such as cellulose, lignin or chitin, and the like.

The polymers can be straight-chain, branched-chain or crosslinked. If they are straight-chain polymers, they advantageously have a mean molecular weight of at least 500.

Preferred classes of straight-chain polymers are: straight-chain polymerisation products having a mean molecular weight of about 500 to about 2,000,000, especially of about 1000 to about 200,000; straight-chain polycondensation products having a mean molecular weight of about 500 to 60,000, particularly of about 1000 to about 30,000; straight-chain polyaddition products having a mean molecular weight of about 1000 to about 40,000, especially of about 2000 to about 20,000; straight-chain products which are obtained by ring-opening polymerisation and which have a mean molecular weight of about 500 to about 40,000, particularly about 1000 to about 20,000; decomposition and transformation products from natural substances having a mean molecular weight of about 500 to about 2,000,000, especially of about 1000 to about 100,000.

The mean molecular weights are determined by known methods, generally by means of vapour pressure osmometry, light scattering or viscosity measurements.

Of particular importance are salts of the formula

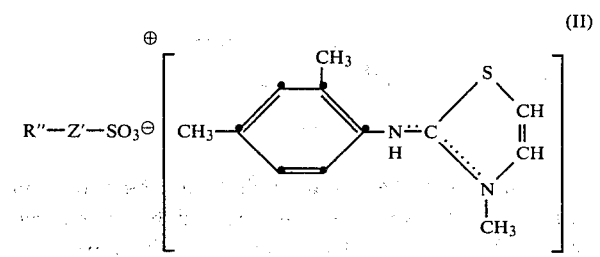

wherein R" is a polymer member of the formula

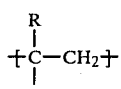

R is hydrogen, chlorine, —CN or C$_1$–C$_4$-alkyl, Z' is the direct bond, —O—, straight-chain or branched-chain alkylene having 1–4 C atoms, phenylene or naphthylene each of which is unsubstituted or substituted by halogen atoms, alkyl or alkoxy groups having 1–4 C atoms or by a group —SO$_3$$^\ominus$M$^\oplus$, or Z' is —CH$_2$O—CH$_2$CH$_2$—, —CH$_2$OCH$_2$CH$_2$O—, —CH$_2$SCH$_2$CH$_2$—, —CH$_2$—S—CH$_2$CH$_2$O—, a ring-substituted group

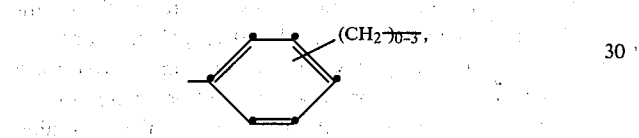

in which the ring is unsubstituted or is substituted by halogen atoms, or by alkyl or alkoxy groups having 1–4 C atoms, or Z' is a group

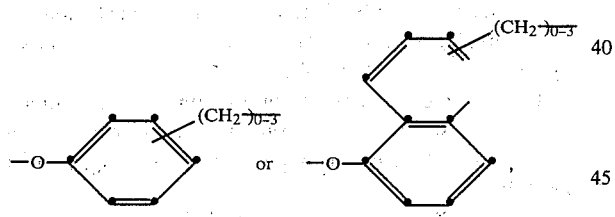

each of which is unsubstituted or substituted by —SO$_3$$^\ominus$M$^\oplus$, or Z' is —COOR$_1$ or —CON(R$_2$)(R$_3$)—, in which R$_1$ is straight-chain or branched-chain C$_3$–C$_8$-alkylene which is unsubstituted or substituted by chlorine or bromine atoms, or interrupted by an oxygen atom, or R$_1$ is cyclohexylene, phenylene, naphthylene, naphthylene substituted by a group —SO$_3$$^\ominus$M$^\oplus$, or it is C$_2$–C$_4$-alkylene-O-phenylene or

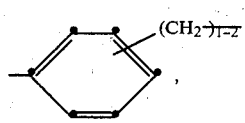

R$_2$ is the direct bond, straight-chain or branched-chain C$_1$–C$_6$-alkylene optionally interrupted by an oxygen atom, or it is straight-chain or branched-chain oxyalkylene having 1–6 C atoms, phenylene, naphthylene, naphthylene substituted by a group —SO$_3$$^\ominus$M$^\oplus$, or it is C$_1$–C$_4$-alkylene-O-phenylene,

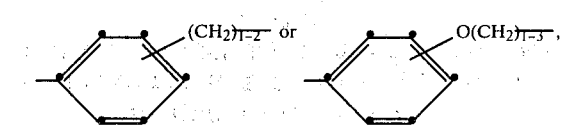

R$_3$ is hydrogen or C$_1$–C$_6$-alkyl, and M$^\oplus$ is hydrogen or

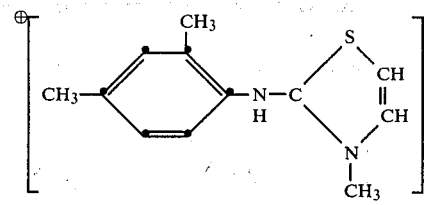

the proportion of cation being at least 5% and preferably 30–100%, relative to the number of recurring structural elements of the polymer.

Preferred polymers of this type are: linear polymers having a mean molecular weight of about 500 to 2,000,000, which contain recurring structural elements of the formula III

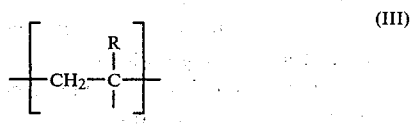

wherein R has the meaning given above, and the proportion of recurring structural elements of the formula III is 0.5 to 95%, relative to the number of recurring structural elements of the polymer; polymers having recurring structural elements of the formula II, recurring structural elements of the formula IV

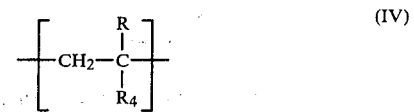

wherein R is hydrogen, chlorine, —CN or C$_1$–C$_4$-alkyl, R$_4$ is hydrogen, halogen, —CON(R$_5$)(R$_6$), —COOH, —COO$^\ominus$Me$^\oplus$, phenyl which is unsubstituted or substituted by chlorine, or R$_4$ is alkyl, alkoxy or alkenyl each having up to 4 C atoms, cyclohexyl, —COO-alkyl having 1–12 C atoms in the alkyl moiety, —COO(CH$_2$)$_x$—OH, —COO-phenyl, —OCO-alkyl having 1–4 C atoms in the alkyl moiety, —OCO-phenyl, —CO-alkyl having 1–4 C atoms in the alkyl moiety, phenoxy or a group

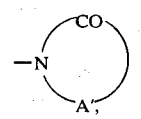

Me is a monovalent metal, x is an integer from 2–6 inclusive, A' is —(CH$_2$)$_3$—, —(CH$_2$)$_5$—, —CO—(CH$_2$)$_2$—, —CO—CH=CH— or

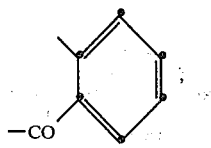

$R_5$ is hydrogen, $C_1$–$C_4$-alkyl, $C_1$–$C_6$-hydroxyalkyl or phenyl, and $R_6$ is hydrogen or $C_1$–$C_4$-alkyl, and optionally structural elements of the formula III, the proportion of recurring structural elements of the formulae III and IV together being 0.5 to 95%, relative to the recurring structural elements of the polymer; crosslinked polymers having recurring structural elements of the formula II, recurring structural elements of the formula V

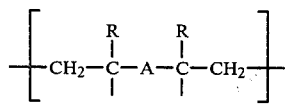 (V)

wherein R is hydrogen, chlorine, —CN or $C_1$–$C_4$-alkyl, A is the direct bond, —O—, —$SO_2$—,

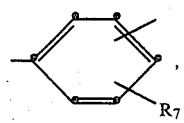

—COO—, —COOCH$_2$, —CONH—, —CONHCH$_2$—, $Me^{2+}(^-OOC)_2$—, $Me^{3+}(^-OOC)_2$ (—OOC— CR—CH$_2$)—, —CONH(CH$_2$)$_y$NHCO—, —COO(CH$_2$)$_x$—OCO— or —COO(CH$_2$)-$_{\frac{1}{2}}$[O—(CH$_2$)$_2$]$_{\overline{1-3}}$OCO—, $R_7$ is hydrogen, ethyl, —$SO_3$H or

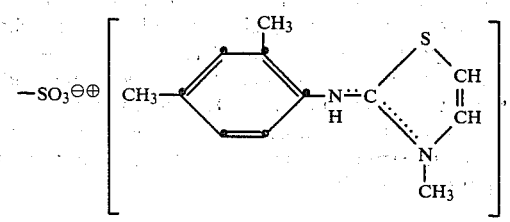

Me is a bi- or trivalent metal, y is an integer from 1–6 inclusive, and x is an integer from 2–6 inclusive, and optionally recurring structural elements of the formula III and/or IV, the proportion of recurring structural elements of the formula V being 0.2–20% and the proportion of recurring structural elements of the formula III and/or IV together being at most 94.5%, relative to the number of recurring structural elements of the polymer.

Alkyl and hydroxyalkyl groups denoted in the above formulae by R, $R_3$, $R_4$, $R_5$ and $R_6$, alkenyl groups denoted therein by $R_4$, as well as alkyl and alkoxy substituents in groups Z and $R_4$, can be straight-chain or branched-chain; they are however preferably straight-chain. Alkyl groups R, $R_5$ and $R_6$ and also alkyl or alkoxy substituents in groups Z preferably contain 1 or 2 C atoms. When Z groups are substituted by halogen atoms, they are in particular chlorine or bromine atoms. Alkylene groups $R_1$ and $R_2$ are preferably unsubstituted, and have 3–5 and 1–5 C atoms, respectively. Alkylene groups $R_4$ and hydroxyalkyl groups, $R_5$ advantageously contain 1–4 C atoms.

The following may be mentioned as examples of mono- to trivalent metals Me: Na, K, Ba, Mg, Ca and Al.

Preferred salts are those of the cation of the formula

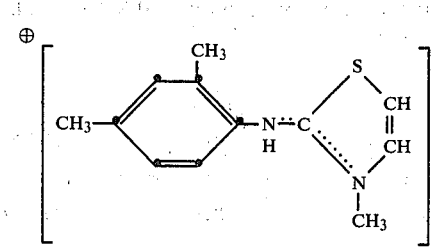

with an anion from the groups comprising polyvinylsulfonic acids, polystyrenesulfonic acids, poly[N-(sulfoalkyl)acrylamide] and sulfonated cation exchangers from styrene and about 8–12 percent by weight of divinyl benzene (crosslinking agent), or sulfonated cation exchangers having macroporous structures.

A further class of preferred polymers are those consisting of recurring structural elements of the formulae VIa to VIe:

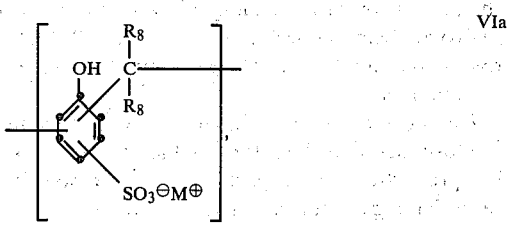 VIa

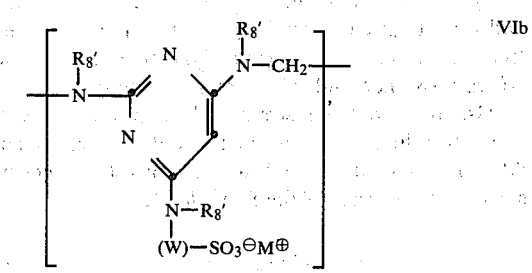 VIb

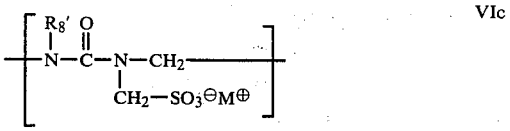 VIc

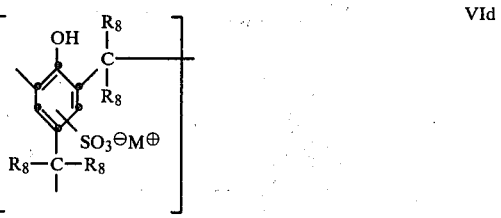 VId oder

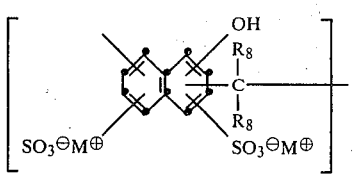 VIe or mixtures thereof, wherein $R_8$ and $R_8'$ are each hydrogen or methyl,
W is

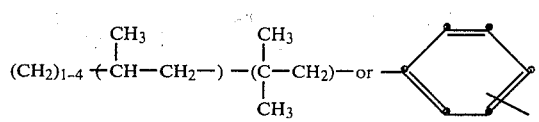

and $M^\oplus$ is hydrogen or the group

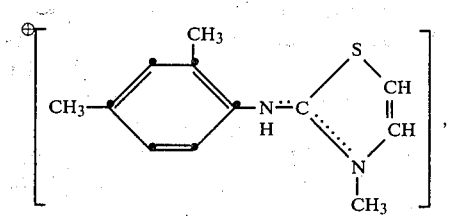

the proportion of the cation $M^\oplus$ where it is other than hydrogen being at least 5%, preferably 30–100%, relative to the number of recurring structural elements of the polymer.

Among the polymers having structural elements of the formulae II to VIe, those which have ion-exchanging properties have a particular importance. Polymer resins having a macroporous structure prove to be especially suitable by virtue of their large internal surface and their high capacity for salt formation with the active substance, and by virtue of the adequate release of active substance under biological conditions.

Also preferred are straight-chain polycondensation products which have a mean molecular weight of about 500 to about 60,000 and which consist of recurring structural elements of the formula VII $$+Y_1-L-Y_2-Q+ \quad \text{(VII)}$$

wherein L is a group

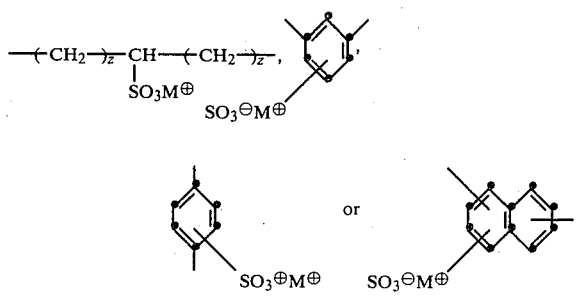

z is the number 1 or 2, z' is nought, 1 or 2, $M^\oplus$ is hydrogen or the group

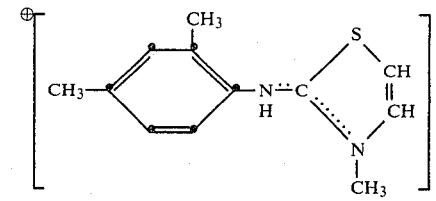

$Y_1$ and $Y_2$ independently of one another are each —OCO—, —COO—, —CONH—, —OCONH— or —NHCONH—, Q is $C_2$-$C_{10}$-alkylene which is optionally branched-chain, or interrupted by —O— or —$NR_8$—, or they are phenylene or naphthylene each of which is unsubstituted or is substituted by halogen atoms, methyl, methoxy or —$SO_3^\ominus N^\oplus$ groups, or they are cyclohexylene,

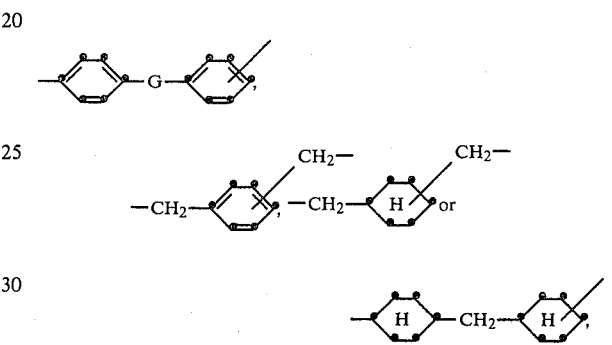

and G is the direct bond, —O—, —$CH_2$—, —$C(CH_3)_2$ or —$SO_2$—, the proportion of the cation $M^\oplus$ where it is other than hydrogen being at least 5%, preferably 30–100%, relative to the number of recurring structural elements of the polymer.

The salts according to the invention can be produced essentially by three methods known per se, namely:

(a) by reacting an optionally crosslinked or branched-chain polymer, which contains laterally bound —$SO_3H$ groups, which are bound directly or by way of a bridge member to the polymer main structure, the proportion of these groups being at least 5% relative to the number of recurring structural elements of the polymer, with a compound of the formula VIII

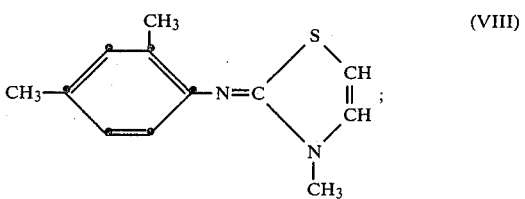 (VIII)

(b) by firstly reacting a monomer, which contains —$SO_3H$— groups bound directly or by way of a —$COOCH_2$— bridge member, with a compound of the formula VIII, and subsequently converting the resulting monomer salt, optionally in the presence of comonomers and/or crosslinking agents, into a polymer, the molar ratio of monomer salt to comonomer and/or crosslinking agent being 1:19 to 1:0; or (c) by reacting a polymer, which contains reactive groups, for example the anhydride, acid chloride, ester, isocyanate or epoxide groups, with at least 5%, relative to the number of recurring structural elements of the polymer, of a compound of the formula IXa or IXb

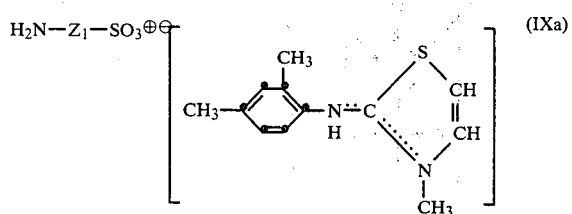 (IXa)

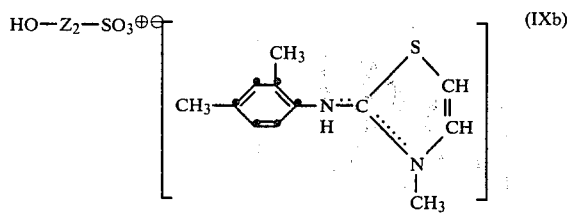 (IXb)

wherein $Z_1$ is the direct bond, straight-chain or branched-chain $C_1$-$C_8$-alkylene which is unsubstituted or substituted by chlorine or bromine or is optionally interrupted by an oxygen atom, or $Z_1$ is cyclohexylene, or phenylene or naphthylene each of which is unsubstituted or substituted by a group $-SO_3M^\oplus$, and $Z_2$ is the direct bond, straight-chain or branched-chain $C_3$-$C_8$-alkylene which is unsubstituted or substituted by chlorine or bromine, or $Z_2$ is cyclohexylene, phenylene or naphthylene each unsubstituted or substituted by a group $-SO_3M^\oplus$, or $Z_2$ is

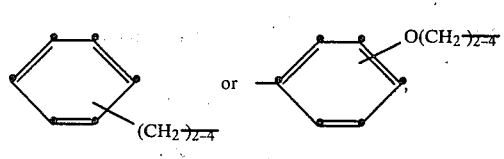

and $M^\oplus$ is hydrogen or

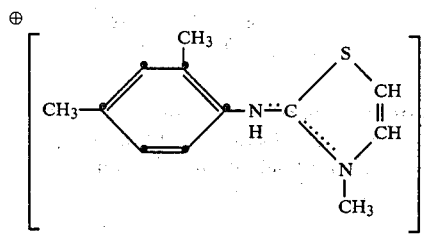

The above reactions are performed advantageously in the presence of a suitable inert solvent, such as dioxane, chloroform, $CH_2Cl_2$, tetrahydrofuran, ethanol, methanol, and so forth. The reaction can be carried out in a homogeneous solution, in a dispersion or in a suspension. Salt formation is effected generally at a temperature of between about 25° and 80° C. The fixation yield can be determined by customary analytical methods, such as by elementary analysis, thin-layer chromatography and gas-chromatography. The conversion of the monomer salts into the corresponding polymers and also the reaction of the salts of the formula IXa or IXb with the defined polymers according to process varient (c) are performed, depending on the type of monomer or polymer, for example by polymerisation, polycondensation or polyaddition, in a manner known per se and with the use of customary solvents, catalysts and/or polymerisation initiators.

The polymers to be used according to the invention are produced, using a process analogous to those described in the foregoing,
(a) by reacting a polymer, which contains recurring structural structural elements of the formula III

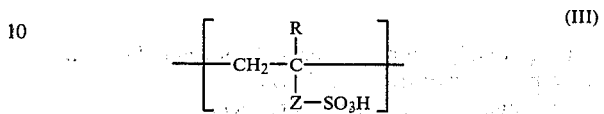 (III)

with a compound of the formula VIII; or
(b) by firstly reacting a monomer of the formula IIa

 (IIa)

with a compound of the formula VIII, and then polymerising the resulting monomer salt of the formula IIb

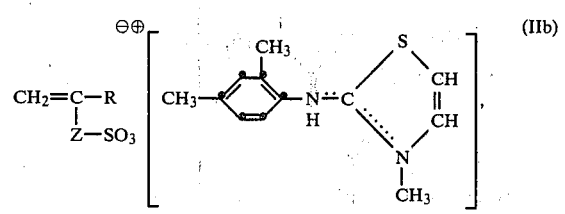 (IIb)

optionally in the presence of comonomers and/or crosslinking agents, the molar ratio of compounds of the formula IIb to comonomers and/or crosslinking agents being 1:19 to 1:0, and R and Z having the meanings defined in the foregoing.

Polymer salts having a mean molecular weight of about 500 to about 2,000,000 can be produced for example by reacting a polymer consisting of recurring structural elements of the formula III, in a ratio of 20:1 to 100:99.5 relative to the number of recurring structural elements of the polymer, with a compound of the formula VIII; or by polymerising a monomer salt of the formula IIb, in a molar ratio of 1:19 to 199:1, with a comonomer of the formula IIa. Polymer salts can also be obtained by reacting a polymer consisting of recurring structural elements of the formula III and 0.5 to 95% of recurring structural elements of the formula IV, in a ratio of 20:1 to 100:99.5 relative to the number of recurring structural elements of the polymer, with a compound of the formula VIII; or by polymerising a salt of the formula IIb, in a molar ratio of 1:19 to 199:1, with a comonomer of the formula IVa $$CH_2=C-R$$
$$\phantom{CH_2=C-}|$$
$$\phantom{CH_2=C-}R_4$$

and optionally a comonomer of the formula IIa.

Finally, polymer salts can be produced either by reacting a polymer consisting of recurring structural elements of the formula III, 0.5–20% of recurring structural elements of the formula V and optionally 75–94.5% of recurring structural elements of the formula IV, in a ratio of 20:1 to 100:99.5 relative to the number of recurring structural elements of the polymer, with a compound of the formula VIII, or by polymerising a monomer salt of the formula IIb, in a molar ratio of 1:19 to 199:1, with a crosslinking agent of the formula Va

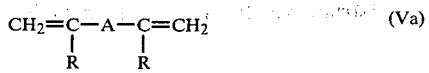

and optionally a comonomer of the formula IVa and/or a comonomer of the formula IIa.

Polymer salts can also be produced (a) by reacting a polymer consisting of recurring structural elements of the formulae VIa' to VIe'

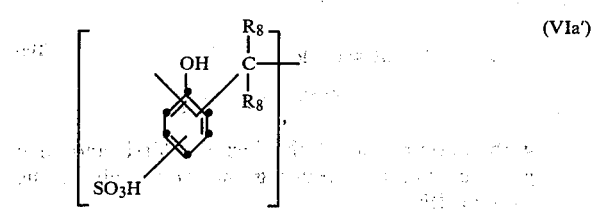

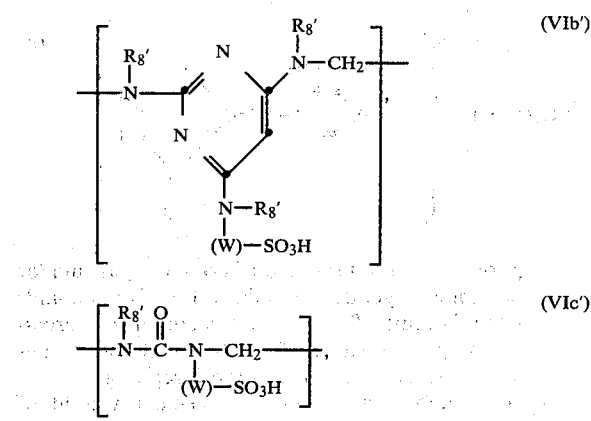

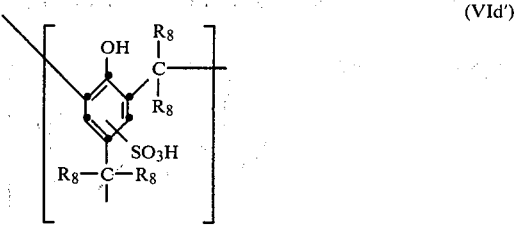

or

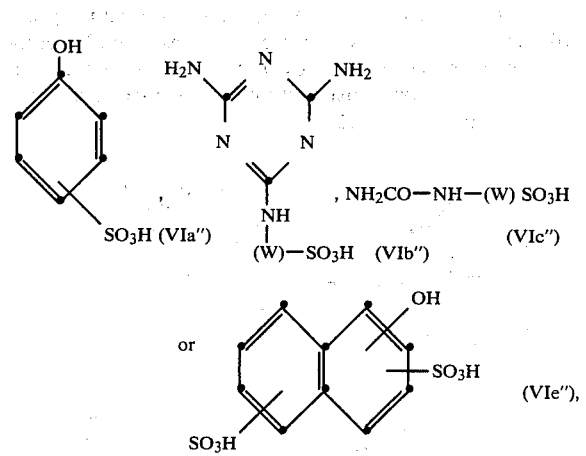

or mixtures thereof, in a ratio of 20:1 to 1:1 relative to the number of recurring structural elements of the formulae VIa, VIb, VIc, VId and VIe, with a compound of the formula VIII; or (b) by firstly reacting a compound of the formula VIa″, VIb″, VIc″ or VIe″ or a mixture of such compounds, with a compound of the formula VIII, and subsequently polycondensing the resulting monomer salt of the formula VIa‴, VIb‴, VIc‴ or VIe‴

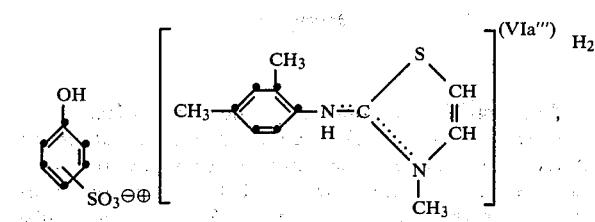

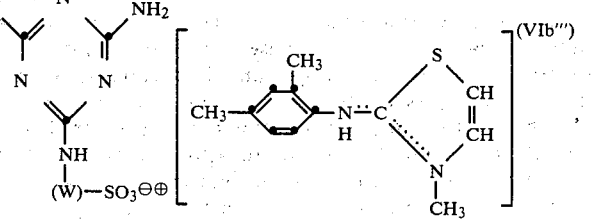

-continued

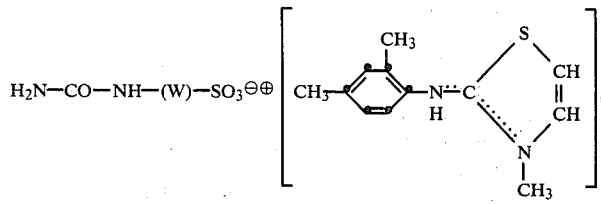 (VIc''')

or 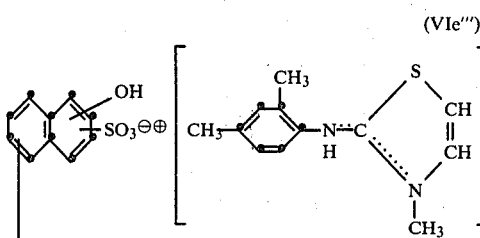 (VIe''')

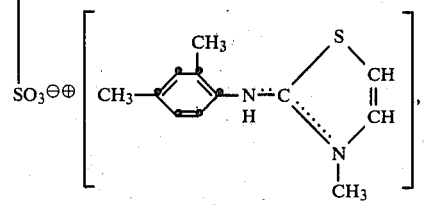

or a mixture of such monomer salts, optionally in the presence of phenol and/or of a compound of the formula VIa'', VIb'', VIc'' or VIe'', with a compound of the formula X $$R_8-\underset{\underset{R_8}{|}}{C}=O, \quad (X)$$

the meanings of $R_8$ and (W) being as defined in the foregoing, and the molar ratio of monomer salt of the formulae VIa''', VIb''', VIc''' and/or VIe''' to compound of the formulae VIa'', VIb'', VIc'', VIe'' and/or phenol being 1:19 to 1:0.

Polymer salts consisting of structural elements of the formula VII are advantageously produced (a) by reacting a polymer consisting of recurring structural elements of the formula VIIa $$+Y_1-L_1-Y_2-Q+, \quad (VIIa)$$

in a ratio of 20:1 to 1:1 relative to the number of recurring structural elements of the polymer, with a compound of the formula VIII; or (b) by firstly reacting a compound of the formula VIIb $$Y_3-L_1-Y_4 \quad (VIIb)$$

with a compound of the formula VIII, and subsequently polycondensing or polyadding the resulting monomer salt of the formula VIIc $$Y_3-L_2-Y_4 \quad (VIIc),$$

optionally in the presence of a compound of the formula VIIb, with a compound of the formula VIId $$Y_5-Q-Y_6 \quad (VIId),$$

in which formulae the symbols have the following meanings:

$L_1$ is a group

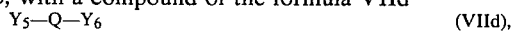

$L_2$ is a group

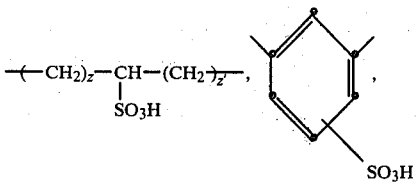

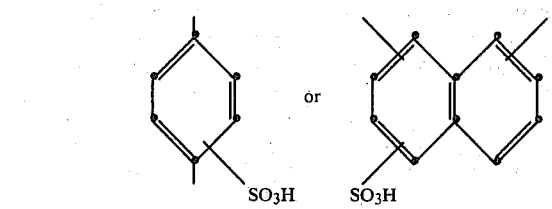

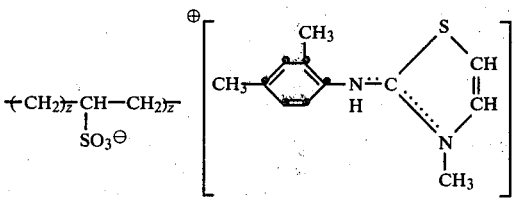

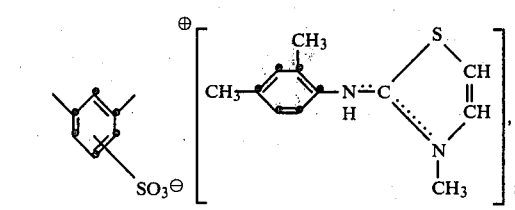

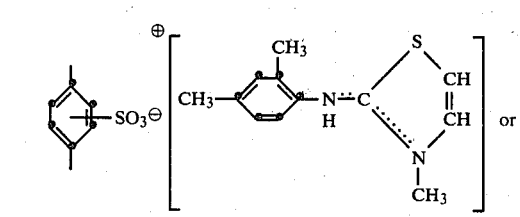 or

-continued

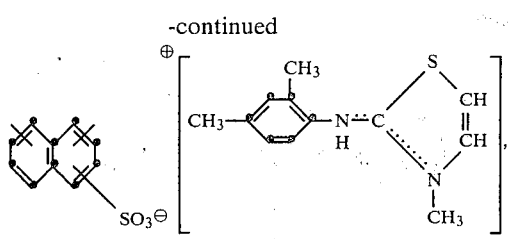

Y₃ and Y₄ independently of one another are each —OH, —NH₂, —COCl, —COOH, —COO-phenyl or —COO-alkyl having 1-3 C atoms in the alkyl moiety, and when Y₃ and/or Y₄ are —OH or NH₂, Y₅ and Y₆ independently of one another are each —COCl, —COOH, —COO-phenyl, —COO-alkyl having 1-3 C atoms in the alkyl moiety or they are each —NCO, and, when Y₃ and/or Y₄ are —COCl, —COOH, —COO-alkyl having 1-3 C atoms in the alkyl moiety or —COOP-phenyl, Y₅ and Y₆ independently of one another are each —OH or —NH₂, Y₁ and Y₂ being as defined in the foregoing, and the molar ratio of compound of the formula VIIc to compound of the formula VIIb being 1:19 to 1:0.

The reactants to be used for the above reactions are known or can be produced by methods known per se. Polymers having laterally-bound —SO₃H groups bound as defined can be produced for example as follows:

(1) By introduction of the —SO₃H groups into an existing linear, branch-chain or crosslinked polymer chain by substitution, condensation or addition reactions, for example by sulfonation with SO₃, H₂SO₄, and the like, sulfochlorination, sulfomethylation, sulfoethylation with vinylsulfonic acids, sulfoalkylation with sulfones or sodium bisulfite addition reaction with double bonds, for example with polyethylene fumarate or butadiene-polymers; or by reaction of polymers having reactive groups, such as anhydride, acid chloride, ester, isocyanate or epoxide groups, for example polyacrylic acid chloride, -methyl ester or -glycidyl ester, with functional sulfonic acids or functional polysulfonic acids which carry hydroxyl or amino groups, or by reaction of HO- or HN-containing polymers with cyclic sulfones.

(2) By synthesis of the polymer chain formed from monomers which contain the —SO₃H group in the free or masked form, for example as salt, whereby the polymer chain can be formed by polymerisation, polyaddition, polycondensation or ring-opening polymerisation, optionally in the presence of suitable comonomers and/or crosslinking agents. Examples for the formation of the polymer chain from suitable monomers are in particular the homo- and copolymerisation of polymerisable sulfonic acids, optionally in the presence of crosslinking agents, as described for example in the U.S. Pat. Nos. 2,983,712 and 2,914,499, and in the German Auslegeschriften (publication after examination) Nos. 1,224,506 and 1,292,129; polycondensation of diols, diamines, amino alcohols, dicarboxylic acids and derivatives thereof or diisocyanates, all containing sulfonic acid groups, with suitable cocondensation components; and polycondensation of sulfonic acids of aromatic hydroxyl compounds, for example phenolsulfonic acids, with aldehydes or ketones, such as formaldehyde.

It is also possible to use as starting polymers sulfated or sulfoalkylated polysaccharides, such as cellulose, amylose, and so forth, ligninsulfonic acids or sulfoalkylated proteins, which can be produced in a manner known per se.

Examples of monomers to be used in process varient (b), as well as of comonomers and crosslinking agents to be concomitantly used if need be, are to be found in the above-mentioned U.S. patent specifications and German Auslegeschriften. Salts of the formulae IXa and IXb can be produced, using customary methods, by reaction of the appropriate amino- or hydroxysulfonic acids with compounds of the formula VIII.

The salts of the formula I are suitable for combating various animal and plant pests. These salts are suitable in particular for combating insects and phytopathogenic mites, for example of the order Lepidoptera, Coleoptera, Homoptera, Heteroptera, Diptera, Acarina, Thysanoptera, Orthoptera, Thysanura, Isoptera, Psocoptera and Hymenoptera. The salts of the formula I are especially suitable for combating zooparasitic lice, mites and ticks, for example Rhipicephalus, Boophilus and Amblyomma. They inhibit the oviposition of fertile eggs and are effective against all development stages.

The polymers having groups of the formula I surprisingly have a stability and long-term action better than those of analogous salts known from the British Pat. No. 1,394,990. The compounds of the formula I are also safer in application than are the free bases.

The polymers having groups of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the salts of the formula I with suitable carriers, optionally with the addition of dispersing agents or solvents which are inert to the active substances.

EXAMPLE 1

218 g of 3-methyl-2-(2',4'-dimethylphenylimino)-4-thiazoline are dissolved in 500 ml of ethanol. There are then introduced, with stirring, 420 g of the ground cation exchanger "Kastel C-300 N" ®. "Kastel C-300 N" is a cation exchanger which is produced by polymerisation of styrene with simultaneous crosslinking with 8% of divinyl benzene and subsequent sulfonation. It contains 48% of water after grinding, and its capacity amounts to 4.6 m equiv. of —SO₃H per gram of anhydrous substance.

The solution with the suspended ion exchanger is stirred until no further 3-methyl-2-(2',4'-dimethylphenylimino)-4-thiazoline is contained in the solvent, a process which requires about 4 hours. The suspension is afterwards centrifuged, the supernatant solvent is separated, and the solid substance is dried at 60° C. in vacuo.

50 parts of the dry product are finally mixed with 10 parts of dispersing agent (sulfite cellulose liquor and sodium lauryl sulfate) and 40 parts of kaolin, and the mixture is finely ground to give a wettable powder having a content of 25% of 3-methyl-2-(2',4'-dimethylphenylimino)-4-thiazoline (WP 25).

EXAMPLE 2

In order to obtain a system free from water, a cation exchanger, which is produced by polymerisation of styrene with simultaneous crosslinking with 8 percent by weight of divinyl benzene and subsequent sulfonation ["Dowex HCR-S" ®, Dow Chemical], is ground, and then dried at 90° C. in vacuo. The exchange capacity of the ion exchanger is 4.7 m equiv. of —SO$_3$H per gram.

180 g of 3-methyl-2-(2',4'-dimethylphenylimino)-4-thiazoline are dissolved in 526 g of Diesel oil, and 180 g of the dried and ground cation exchanger are introduced portionwise into this solution. To the resulting suspension are added dropwise 24 g of methanol within 15 minutes. An exothermic reaction occurs, and the reaction mixture is held for 3 hours at 50° C. with continuous stirring. To stabilise the suspension, 100 g of oleyl polyglycol ether and 10 g of bentone are stirred in. The stable suspension thus obtained contains per liter 180 g of 3-methyl-2-(2',4'-dimethylphenylimino)-4-thiazoline.

EXAMPLE 3

Action against ticks (A) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The test tubes were then sealed with a standardised cotton plug, and inverted so that the active-substance emulsion could be absorbed by the cotton wool. The evaluation in the case of the adults was made after 2 weeks and in the case of the larvae after 2 days. There were two repeats for each test.

(B) *Boophilus microplus* (larvae)

With a dilution series analogous to that of Test A, tests were carried out with 20 sensitive larvae and OP-resistant larvae, respectively (resistance is with respect to diazinon compatibility).

Salts according to Example 1 were effective in these tests against adults and larvae of *Rhipicephalus bursa* and against sensitive and OP-resistant larvae, respectively, of *Boophilus microplus*.

EXAMPLE 4

Action against ticks (inhibition of oviposition)

The test insects used were females of cattle ticks, *Boophilus microplus*, which had sucked themselves full. 10 ticks of a resistant strain and 10 ticks of a normally sensitive strain were treated per concentration. The ticks were immersed for a short time in the respective aqueous emulsions or aqueous solutions of the salts of the compounds to be tested. The ticks were then fixed on plates by means of double adhesive tape, and subsequently kept in an air-conditioned chamber under constant conditions. An evaluation made after three weeks established that a total inhibition of the oviposition of fertile eggs had resulted.

Even at low concentrations, the substances according to Example 1 had a complete inhibitory effect.

What is claimed is:

1. A salt formed from a cation of the formula

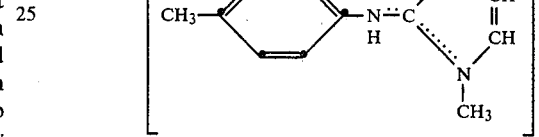

and an anion polymer selected from the group consisting of polyvinylsulfonic acids, polystyrenesulfonic acids, poly[N-(sulfoalkyl)-acrylamide], sulfonated cation exchangers from styrene and about 0.5–12 percent by weight of divinyl benzene (crosslinking agent) and sulfonated cation exchangers having macroporous structures, the proportion of the cation being at least 5% relative to the number of recurring structural elements of the polymer.

2. A salt according to claim 1, wherein said anion is a polystyrenesulfonic acid.

* * * * *